United States Patent [19]

Flores Rivera

[11] Patent Number: 4,792,445

[45] Date of Patent: Dec. 20, 1988

[54] HIGHLY STABLE FREE IODINE IODOPHOR COMPOSITIONS, PROCESS FOR PREPARING SAME AND PROCESS FOR USING SAME

[76] Inventor: Mario Flores Rivera, calle San Salvador #457, San Salvador, El Salvador

[21] Appl. No.: 47,511

[22] Filed: May 6, 1987

Related U.S. Application Data

[63] Continuation of Ser. No. 744,666, Jun. 14, 1985, abandoned, which is a continuation of Ser. No. 549,106, Nov. 7, 1983, abandoned.

[51] Int. Cl.[4] ............... A01N 59/12; A61K 31/74; C11D 3/48
[52] U.S. Cl. .................................. 424/78; 252/106; 424/150
[58] Field of Search ................ 424/150, 78; 252/106

[56] References Cited

U.S. PATENT DOCUMENTS

| | | | |
|---|---|---|---|
| 344,056 | 6/1886 | Shilton | 424/150 |
| 703,091 | 6/1902 | Spencer | 340/403 |
| 1,004,282 | 9/1911 | Lacroix | 187/3 |
| 1,467,614 | 9/1923 | Eads | 132/73 |
| 2,840,510 | 6/1958 | Katz et al. | 252/106 |
| 3,028,299 | 4/1962 | Winicov et al. | 424/150 |
| 4,113,857 | 9/1978 | Shetty | 424/80 |
| 4,271,149 | 6/1981 | Winicov et al. | 424/78 |
| 4,288,428 | 9/1981 | Foll et al. | 424/150 |
| 4,526,751 | 7/1985 | Gartner | 424/150 |

FOREIGN PATENT DOCUMENTS 1191970  5/1970  United Kingdom ............... 424/150

OTHER PUBLICATIONS

CTFA Cosmetic Ingredient Dictionary, 3rd ed., The Cosmetic Toiletry and Fragrance Assn, Inc. Publishers, p. 182 (1982).

Primary Examiner—Douglas W. Robinson
Attorney, Agent, or Firm—Sughrue, Mion, Zinn, Macpeak, and Seas

[57] ABSTRACT

A highly stable free iodine iodophor composition useful as a bactericide or fungicide comprising: (a) an ether-nonyl polyglycol ethoxylate having an ethylene oxide mole number greater than 4; (b) elemental iodine; (c) potassium iodine; (d) water; and (e) optionally, any other agriculturally acceptable liquid carrier or diluent.

16 Claims, No Drawings

HIGHLY STABLE FREE IODINE IODOPHOR COMPOSITIONS, PROCESS FOR PREPARING SAME AND PROCESS FOR USING SAME

This is a continuation of application Ser. No. 744,666 filed June 14, 1985, now abandoned which is a continuation of application Ser. No. 549,106 filed Nov. 7, 1983, now abandoned.

FIELD OF THE INVENTION

The present invention relates to iodophor compositions containing highly stable free iodine, a process for preparing same and a process for using same as a fungicide or bactericide.

BACKGROUND OF THE INVENTION

Fungicidal compositions based on copper salts are well known to kill a wide variety of fungus on contact. However, these preparations act only on the external surfaces of plants and are not absorbed by plant tissues. Thus, these compositions only control the external fungi manifestation of infected vegetation while leaving unaffected the internal manifestation. That is, vegetation infected by fungus suffer internal damage, for example, the plugging of the food conducting tissues at the union between the stock and scion which quickly kills the vegetation. Hence, it is desired that a fungicide not only kill fungi on the surface of the vegetation but also enter the plant system and be active therein.

The term "vegetation" herein is intended to mean any plant, cane, vine, shrub, bush, tree or any vegetation in general.

Attempts have been made to find a satisfactory method for effectively combating fungi such as coffee tree rust (*Hemileia vastatrix Berk.*). However, known treatments have not achieved a satisfactory degree of success beyond a partial control of the external manisfestation of the fungi.

Various iodophor compositions are well known in the art to be suitable as bactericides and fungicides. More specifically, U.S. Pat. No. 4,271,149 teaches germicidal iodine compositions comprising an aqueous solution of iodine, iodide ion, iodate ion and an organic substance which slowly reacts with iodine, for example, a surface active agent such as ethoxylates of alkyl phenols. In such compositions, the free iodine level is maintained for extended periods of time by the presence of both an iodate ion and a buffer to control the pH within the range of 5-7. Such compositions are disadvantageous in that they require both the addition of an iodate ion and a buffer for maintenance of the pH range.

U.S. Pat. No. 4,288,428 teaches an iodophorous disinfecting composition comprising an iodophor in the form of an alkyl phenoxy poly(ethyleneoxy)-ethanol-iodine complex. This iodophor complex contains 5-10% by weight urea and an acid in an amount sufficient to maintain a pH between 1-5. This composition is disadvantageous in that it requires the use of both urea and an acid to control the pH as well as a solvent.

U.S. Pat. No. 4,113,857 discloses a method for producing an organic iodophor germicidal composition comprising reacting an organic iodophor forming compound, for example, nonyl phenoxy poly(ethyleneoxy)-ethanol with an iodine adding agent, for example, potassium iodide, and hydriodic acid in the presence of an oxidizing stabilizer such as potassium iodate. This iodophor preparation is disadvantageous since it requires the use of hydriodic and an iodate.

U.S. Pat. No. 344,056 discloses a disinfectant consisting of a mixture of ammonium chloride, potassium iodide dissolved in water and iodine. However, this composition is disadvantageous since it is not very stable.

SUMMARY OF THE INVENTION

An object of the present invention is to provide a highly stable free iodine iodophor composition that does not require the use of a buffer solution to maintain the pH so as to prevent reduction of the free iodine into iodide.

Another object of the present invention is to provide a fungicide which is effective against internal fungi infections of vegetation.

An additional object of the present invention is to provide a method for producing the above-described iodophor composition.

A still further object of the present invention is to provide a method of use of the iodophor composition as a bactericidal, fungicidal, or disinfectant composition.

The above objects of the present invention have been met in one embodiment by an iodophor composition comprising:

(a) an ether-nonyl polyglycol ethoxylate having an ethylene oxide mole number greater than 4 represented by the following formula:

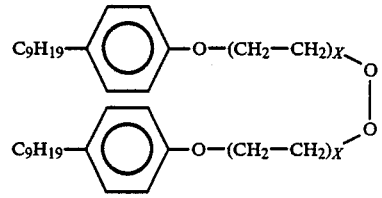

X = number of moles of ethylene oxide (b) elemental iodine;
(c) potassium iodide; and
(d) water; and
(e) optionally, any other agriculturally acceptable liquid carrier or diluent.

DETAILED DESCRIPTION OF THE INVENTION

As stated above, the present invention relates to a highly stable free iodide iodophor composition comprising (a) an ether-nonyl polyglycol ethoxylate having an ethylene oxide mole number greater than 4; (b) elemental iodine; (c) potassium iodide; (d) water; and (e) optionally, any other agriculturally acceptable liquid carrier or diluent.

The stability of the iodophor composition of the present invention is obtained by the addition, to a free iodine solution, of the ether-nonyl polyglycol ethoxylate having an ethylene oxide mole number greater than 4. That is, the oxidation of elemental iodine through potassium iodide is stabilized by the non-ionic compound, i.e, ether-nonyl polyglycol ethoxylate having an ethylene oxide mole number greater than 4. While the upper limit of the ethylene oxide mole number is not critical, a typical upper range is 30, a preferred range is up to 10. Examples of such ether-nonyl polyglycol ethoxylates useful in the present invention include Hostapal 3634 (ethylene oxide mole number of 10), Arkopal N-090

(ethylene oxide mole number of 9), Arkopal N-080 (ethylene oxide mole number of 8), Arkopal N-100 (ethylene oxide mole number of 10), Arkopal N-060 (ethylene oxide mole number of 6), Arkopal N-110 (ethylene oxide mole number of 11), Arkopal N-130 (ethylene oxide mole number of 13), Arkopal N-150 (ethylene oxide mole number of 15), Arkopal N-230 (ethylene oxide mole number of 23) and Arkopal N-300 ethylene oxide mole number of 30). When the ethylene oxide mole number increases, the solubility of the ether-nonyl polyglycol ethoxylate is also increased. Preferably, Hostapal 3634, Arkopal N-060 and Arkopal N-100 are employed in the present invention.

The ether-nonyl polyglycol ethoxylate having an ethylene oxide mole number greater than 4 may be dissolved in, e.g., hard water or soft water at a temperature of about 70° C., preferably not less than 60° C., although higher temperatures, i.e., up to just less than the boiling point can also be used. The ether-nonyl polyglycol ethoxylate having an ethylene oxide mole number greater than 4 cannot be used in water solutions containing more than 1.5 ppm chlorine since the stability thereof is adversely affected.

A useful weight ratio of elemental iodine to potassium iodide is in the range of 1:1.01 to 1:1.05, preferably 1:1.03.

It is preferable that the weight ratio of the ether-nonyl polyglycol ethoxylate having an ethylene oxide mole number greater than 4 to the combined weight of the elemental iodine and the potassium iodide is 3:1 to 20:1, more preferably 6:1.

The iodophor composition of the present invention is prepared by first dissolving elemental iodine and potassium iodide in water, and optionally with any other agriculturally acceptable diluent, at a temperature of not more than about 25° C., preferably not less than 20° C. Then, the mixture is diluted in 1 to 4 parts water or any other agriculturally acceptable diluent (Solution A).

Next, an ether-nonyl polyglycol ethoxylate having an ethylene oxide mole number greater than 4 is dissolved at a ratio of not more than 1.25 parts (w/w) ether-nonyl polyglycol ethoxylate having an ethylene oxide mole number greater than 4 to 1.0 part (w/w) water at a temperature of 60° to 70° C. under agitation so as to achieve a concentration of preferably 55% by weight of ether-nonyl polyglycol ethoxylate having an ethylene oxide mole number greater than 4. Thereafter, the solution is allowed to cool to a temperature of 20°-25° C. (Solution B).

Then, Solution A and Solution B are slowly mixed together under agitation and thoroughly mixed so as to provide a weight ratio of the ether-nonyl polyglycol ethoxylate having an ethylene oxide mole number greater than 4 to the combined weight of the elemental iodine and the potassium iodide of 3:1 to 20:1, preferably about 6:1.

The resulting iodophor composition can be stably stored for extensive periods of time, e.g., more than two years, when stored in, for example, an amber stained glass or plastic opaque container at room temperature (25° C. to 30° C.) without loss of fungicidal, bactericidal or disinfectant activity, as shown in the following Table.

TABLE 1

| TEST | Days 8 | Days 30 | Days 60 | Days 120 | Days 240 | Days 480 | Days 720 |
|---|---|---|---|---|---|---|---|
| ρ | + | + | + | + | + | + | + |
| α | + | + | + | + | + | + | + |
| Stability | + | + | + | + | + | + | + |
| Separation | + | + | + | + | + | + | + |

+ = good
− = bad
ρ: is the density of the composition determined by measurements of mass and volume.
α: is the viscosity of the composition determined by a viscometer (Cannon-Fenske)
Stability: is the stability of the composition determined by testing the bactericidal and fungicidal effectiveness of the composition
Separation: is a determination of the stability of the composition evaluated by visually comparing color and translucence.

In Table 1, samples of the composition of this invention were stored and analyzed after a period of 8 days, 30 days, 60 days, 120 days, 240 days, 480 days and 720 days. The results in Table 1 indicate that no substantial changes were seen in the stability of free iodine in the compositions of the present invention.

The iodophor composition of the present invention is particularly suitable for use on various plants that are infected with various fungi. For example, coffee trees infected with *Hemileia vastatrix Berk;* or citric trees infected with "Foot Rot" *Phytophthora parasitica Dast.,* or *Phythophthora citrophthora.*

In addition, the iodophor composition of the present invention is useful for killing various fungi and bacteria on fresh foods and vegetables. For example, the composition of this invention is effective against the following bacteria: Bacillus sp.; Staphyloccoccus sp.; Coliphorms; Candida sp.; *Salmonella typhi; E. coli; Shigella B.; Proteus vulgaris; Proteus mirabilis; Pseudomonas aeruginosa; Proteus morgani; Proteus rettger;* Micobacterium; and Tuberculossum; as well as the following fungi: *Septobasidium pseudopedicillatum Baurt., Collectrichum gloesporiodes* or *Elsinoe Fawcetti Bit.*

Treatment with the iodophor composition of the present invention may be effective in a variety of ways such as spraying, brushing, washing or immersion.

The iodophor composition of the present invention can be used in its original concentration by brushing or by any other application method directly to the trunk and branches of trees. Pruning cuts and other bark openings can also be treated with the composition of the present invention without any phytotoxic effects. These types of treatment are rapidly effective.

It is preferable that vegetation is sprayed with an aqueous solution of from 2% to 100% (v/v), preferably 2 to 5% (v/v), of the iodophor composition of the present invention. When the amount used is below 2% (v/v), the effectiveness is decreased.

As a systemic solution, the iodophor composition of the present invention is quickly absorbed through the leaves and bark of trees without danger of being washed out by rain, even if it rains about 3 to 4 hours after application. In addition, since there is no reduction of free iodine in the composition of the present invention, there is no danger of phytotoxic effects.

The time most appropriate for treatment using the iodophor composition of this invention depends upon the time of fungal attack. It is preferable that the first treatment of the composition of the present invention occur about 30 days before the rainy season starts. Of course, this will vary depending upon the geographical location of the trees. At this time, the treatment will kill, by contact, the fungi endospores as a preventative treatment and at the same time will stimulate flowering, fructification and the growing of new stems as a result of the systemic action of the composition of the present invention in controlling the internal disease manifestation.

It is preferred that a second treatment be made in the middle of the rainy season. At this time, any new fungus attack will be combated and again plant growth will be stimulated.

The iodophor composition of the present invention is also suitable for sterilizing fruits and fresh vegetables. Once the fruit is picked from the tree it is susceptible to the invasion of microorganisms that cause rotting. At the same time, pathogenic bacteria can be picked up by contact with contaminated soil or water. In addition, blue or green mold, Penicillium sp., or stem end rot caused by *Diaphorte citri* or *Diplodia natalensis* can also infect the fruit. These microorganisms are effectively destroyed by the iodophor composition of the present invention. Spray application is recommended to treat leaves or other soft vegetables without damaging or impairing appearance.

The following examples are illustrative of the present invention and are in no way intended to limit the scope thereof.

EXAMPLE 1

The iodophor composition of the present invention used as a spray, three gallons of the composition as defined below diluted (v/v) in 57 gallons of water, was sufficient to cover one hectare of a coffee plantation.

|  | %/W |
| --- | --- |
| Hostapal 3634 | 1.3177 |
| IK | 0.0922 |
| I | 0.0896 |
| $H_2O$ | 98.5005 |
|  | 100.0000 |

A hectare of coffee trees infected with *Hemileia vastatrix Berk*, located in El Salvador, Central America, was treated with the above 5% (v/v) solution of the iodophor composition of the present invention in April, i.e., 30 days before the rainy season began. The rainy season in El Salvador lasts for about 6 months. A second hectare of coffee trees infected with *Hemileia vastatrix Berk* was left untreated as a control.

The fungus on the surface of the treated trees was killed within 30 days after the treatment and fructification, flowering and the growing of new stems was stimulated thereafter. The fungus prevention effect of the single treatment with the iodophor composition of the present invention lasted 72 days. In contrast, the untreated coffee trees remained infected with the fungus and damage to the trees continued.

EXAMPLE 2

The iodophor composition of the present invention can be used to combat fungi in several citric varieties and as shown below can be effective to control and cure "Foot Rot" disease caused by *Phytophthora parasitica Dast.* and *Phytophthora citrophthora.*

A solution of 5% (v/v) of the iodophor composition of Example 1 was sprayed on one hectare of persic lemon trees infected with "Foot Rot". The aqueous solution acted on the fungi endospores on the bark and leaves of the trees within a few days and was absorbed by the tree system where it acted to combat the internal fungi manifestation affecting the conducting tissues. Persic lemon trees not treated with the composition of the present invention and used as a control were killed by the "Foot Rot".

The iodophor composition of the present invention was also used in its original concentration by brushing it directly on the trunk and branches of persic lemon trees as well as a cover on pruning cuts.

Sap leakage through damaged bark stopped in the treated persic lemon trees after about 10 to 20 days from the date of treatment. Abundant buds, new leaves and stems were also observed in the treated trees and early fruit dropping was reduced which increased the yield of fruit. In contrast, new leaves and stems were not observed in the untreated trees used as a control.

EXAMPLE 3

An aqueous solution of 2% (v/v) of the iodophorous composition of the present invention, as defined below, in water was sprayed on different fresh fruits and vegetables, i.e., citric fruit, bananas, tomatoes, lettuce, avocados, cucumbers, potatoes, cabbage and carrots on conveyor tables, at handling times or in wash dipping baths.

|  | %/W |
| --- | --- |
| Hostapal 3634 | 0.52708 |
| IK | 0.03688 |
| I | 0.03584 |
| $H_2O$ | 99.40020 |
|  | 100.00000 |

The solution destroyed the fungi and bacteria and thus sterilized the fruit as shown in Table 2 below.

TABLE 2

| TIME OF INSPECTION AFTER TREATMENT | TREATED | UNTREATED | ADDITIONAL OBSERVATIONS |
| --- | --- | --- | --- |
| 24 Hours | No signs of fungal and/or bacterial infestation. | No signs of bacterial infestation. | Some of the untreated fruit was softer than the treated ones. |
| 48 Hours | No signs of fungal growth. No signs of rotting. | Signs of rotting and spots of fungal growth. | Untreated fruit and vegetables started to rot. |
| 72 Hours | No signs of fungal or bacterial growth. | Fungi and bacteria colonies present. Rotting process well established. | Treated fruit was firm and clean. No fungal spots observed. Untreated fruit showed large colonies of *Aspergillus, Penicil-* |

TABLE 2-continued

| TIME OF INSPECTION AFTER TREATMENT | TREATED | UNTREATED | ADDITIONAL OBSERVATIONS |
|---|---|---|---|
| | | | *lium* Green and white stains. Bananas were the most affected. |
| 5 Days | No signs of fungal and/or bacterial infestation. Texture changes. Fruit soft. | Rotting process established. Bacteria and fungi established. | Treated fruit was clean and acceptable. Untreated fruit were not acceptable. |

A low dosage of the iodophor composition of the present invention used for sterilization purposes insures that there is no danger of poisoning by animals or humans after ingestion of the treated fruit or vegetables. All of the fruits and vegetables treated lasted longer, were free of rot and did not act as vectors for viruses or bacteria that cause infectious diseases.

EXAMPLE 4

The bactericidal effectiveness of a 10% (v/v) solution of the composition of the present invention, as defined below, was measured in vitro against bacteria in the following manner. Various bacteria, i.e., *Proteus vulgaris, Proteus morgani, Proteus mirabilis, Proteus rettgeri, Pseudomonas aeruginosa, Shigella B., Salmonella typhi,* and *Microbacteria tuberculossum,* were grown on glass slides and treated with the composition of the present invention and evaluated at various time intervals by counting the bacteria and fungi.

| | %/W |
|---|---|
| Hostapal 3634 | 2.6354 |
| IK | 0.1844 |
| I | 0.1792 |
| H₂O | 97.0010 |

-continued

| | %/W |
|---|---|
| | 100.0000 |

The results are shown in Table 3 below.

TABLE 3

| Dilution | 5 minutes after bacterial planting | 10 minutes after bacterial planting | 20 minutes after bacterial planting |
|---|---|---|---|
| 1:10 | No bacteria | No bacteria | No bacteria |

EXAMPLE 5

The bactericidal and fungicidal effectiveness of the composition of Example 4 was measured in situ on tomatoes, cabbages and cucumbers which were inoculated with pathogenic bacteria and fungi 5 minutes and 24 hours after first being treated with a 10% (v/v) solution of the composition of the present invention. The results are shown in Table 4 below.

TABLE 4

| | Bacillus sp. | Staphyloccus sp. | Collyphorm | Penicillum sp. | Candida sp. | Aspergillus sp. |
|---|---|---|---|---|---|---|
| Untreated (observed at 24 hours) | 430,000* | 143,000 | 450,000 | abundant growth | abundant growth | abundant growth |
| Inoculated after 5 min. (observed at 24 hours) | no growth | no growth | no growth | no growth | no growth | no growth |
| Inoculated after 5 min. (observed at 48 hours) | no growth | no growth | no growth | reduced growth | reduced growth | reduced growth |
| Inoculated after 5 min. (observed at 72 hours) | no growth | no growth | no growth | reduced growth | reduced growth | reduced growth |
| Inoculated after 24 hr (observed at 24 hours) | no growth | no growth | no growth | no growth | no growth | no growth |
| Inoculated after 24 hr (observed at 48 hours) | 30,000 | no growth | 2,000 | reduced growth | reduced growth | reduced growth |
| Inoculatd after 24 hr (observed at 72 hours) | 35,000 | no growth | 5,000 | reduced growth | reduced growth | reduced growth |

*bacterial cells/ml

While the invention has been described in detail and with reference to specific embodiments thereof, it will be apparent to one skilled in the art that various changes and modifications can be made therein without departing from the spirit and scope thereof.

I claim:

1. A highly stable free iodine iodophor composition comprising, in admixture:
   (a) an ether-nonyl polyglycol ethoxylate having an ethylene oxide mole number greater than 4 and up to 30;
   (b) elemental iodine;
   (c) potassium iodide; and
   (d) an agriculturally acceptable liquid carrier or diluent, wherein the weight ratio of elemental iodine to potassium iodide is in the range of about 1:1.01 to 1:1.05, wherein the weight ratio of the ether-nonyl polyglycol ethoxylate to the combined weight of the elemental iodine and the potassium iodide is about 3:1 to 20:1 and wherein the agriculturally acceptable carrier or diluent is water.

2. The highly stable free iodine iodophor composition as claimed in claim 1, wherein said ether-nonyl polyglycol ethoxylate has an ethylene oxide mole number up to 10.

3. The highly stable free iodine iodophor composition as in claim 1 wherein said ether-nonyl polyglycol ethoxylate is selected from the group consisting of those having an ethylene oxide mole number of 10, an ethylene oxide mole number of 9, an ethylene oxide mole number of 8, an ethylene oxide mole number of 6, an ethylene oxide mole number of 11, an ethylene oxide mole number of 13, an ethylene oxide mole number of 15, an ethylene oxide mole number of 23 and an ethylene oxide mole number of 30.

4. The highly stable free iodine iodophor composition as in claim 1 wherein the weight ratio of elemental iodine to potassium iodide is 1:1.03.

5. The highly stable free iodine iodophor composition as in claim 1 wherein the weight ratio of the ether-nonyl polyglycol ethoxylate to the combined weight of the elemental iodine and the potassium iodide is 6:1.

6. A process for preparing a highly stable iodine iodophor composition comprising the steps of:
   (1) dissolving elemental iodine and potassium iodide in water at a weight ratio of elemental iodine to potassium iodide of 1:1.01 to 1:1.05 and at a temperature of not more than about 25° C. and diluting the resuting mixture in 1 to 4 parts water or other agriculturally acceptable diluent;
   (2) dissolving an ether-nonyl polyglycol ethoxylate having an ethylene oxide mole number greater than 4 and up to 30 in water at a ratio of not more than 1.25 parts (w/w) ether-nonyl polyglycol ethoxylate to 1 part (w/w) of water at a temperature of about 60°–70° C. under agitation;
   (3) cooling the resulting solution of step (2) to a temperature of about 20° to 25° C.;
   (4) mixing the resulting solutions of steps (1) and (3) under agitation so as to provide a weight ratio of the ether-nonyl polyglycol ethoxylate having an ethylene oxide mole number greater than 4 and up to 30 to the combined weight of the elemental iodine and the potassium iodide of 3:1 to 20:1.

7. The process of claim 6 wherein said ether-nonyl polyglycol ethoxylate has an ethylene oxide mole number up to 10.

8. The process of claim 6 wherein said ether-nonyl polyglycol ethoxylate is selected from the group consisting of those having an ethylene oxide mole number of 10, an ethylene oxide mole number of 9, an ethylene oxide mole number of 8, an ethylene oxide mole number of 6, an ethylene oxide mole number of 11, an ethylene oxide mole number of 13, an ethylene oxide mole number of 15, an ethylene oxide mole number of 23 and an ethylene oxide mole number of 30.

9. A process for using a highly stable free iodine iodophor composition of claim 1 as a bactericidal and fungicidal agent comprising treating vegetation with a bactericidal effective amount or fungicidal effective amount of the composition of claim 1.

10. The process of claim 9, wherein said composition is used in a concentration of from about 2 to 100% (v/v).

11. The process of claim 9, wherein said composition is used in a concentration of from about 2 to 5% (v/v).

12. The process of claim 9, wherein said treating is by spraying, brushing, washing or immersing said composition onto said vegetation.

13. The process of claim 9, wherein said vegetation is selected from the group consisting of coffee trees and citric trees.

14. The process of claim 9, wherein said vegetation is fruit or vegetables.

15. The process of claim 13, wherein said coffee trees are protected against *Hemileia vastatrix Berk.*

16. The process of claim 13, wherein said citric trees are protected against *Phytophthora parasitica Dast.* and *Phytophthora citrophthora.*

* * * * *